United States Patent [19]

Brownlie et al.

[11] Patent Number: 4,487,600
[45] Date of Patent: Dec. 11, 1984

[54] ADJUSTABLE SUCTION DEVICE FOR MEDICAL USE

[76] Inventors: Alan W. Brownlie, W. Lake Rd., Skaneateles, N.Y. 13152; Roger D. Spier, 77 Nelson St., Auburn, N.Y. 13021

[21] Appl. No.: 521,849

[22] Filed: Aug. 10, 1983

Related U.S. Application Data

[63] Continuation-in-part of Ser. No. 319,259, Nov. 9, 1981, abandoned.

[51] Int. Cl.³ ............................................. A61M 1/00
[52] U.S. Cl. ..................................... 604/35; 604/119; 604/93; 433/95
[58] Field of Search ............... 433/91, 95, 96; 15/418, 15/419; 604/43, 48, 40, 35, 118, 119, 73, 902, 93, 118, 131, 173, 181, 264; 137/625.3; 239/539, 541, 586; 27/24 R, 24 A

[56] References Cited

U.S. PATENT DOCUMENTS

| | | | |
|---|---|---|---|
| 1,140,462 | 5/1915 | Johnson | 15/419 X |
| 1,188,180 | 6/1916 | Kells | 128/350 R |
| 1,531,213 | 3/1925 | Nimmer | 604/249 |
| 3,308,825 | 3/1967 | Cruse | 27/24 R |
| 3,416,532 | 12/1968 | Grossman | 128/276 |
| 3,645,497 | 2/1972 | Nyboer | 128/276 |
| 4,204,328 | 5/1980 | Kutner | 15/418 |
| 4,451,257 | 5/1984 | Atchley | 433/95 |

FOREIGN PATENT DOCUMENTS 350404  7/1937  Italy ..................................... 604/93

Primary Examiner—C. Fred Rosenbaum
Assistant Examiner—J. L. Kruter
Attorney, Agent, or Firm—Bruns & Wall

[57] ABSTRACT

An adjustable, disposable suction device that is particularly adapted for medical use. The device is used for removing excess blood or body fluids from an open incision during surgery and is constructed so that it can drain the fluids from a point source or from a larger general area. In the latter case the device can be adjusted to control how much fluid is removed in a given period of time. The device is essentially comprised of a handle, a rigid outer tube formed with an oblique bend and a coacting flexible inner tube. The outer tube is connected at one end to the handle and has a plurality of longitudinally spaced radial apertures adjacent its free end. The flexible inner tube is positioned with a sliding fit in the rigid tube. The inner tube is open at its outer or free end but is otherwise imperforate. With this arrangement, the inner tube can be moved longitudinally within the outer tube to block all of the outer tube apertures or selectively open some or all of them.

In a second embodiment the outer tube is larger in diameter allowing passage of fluids between the tubes.

8 Claims, 16 Drawing Figures

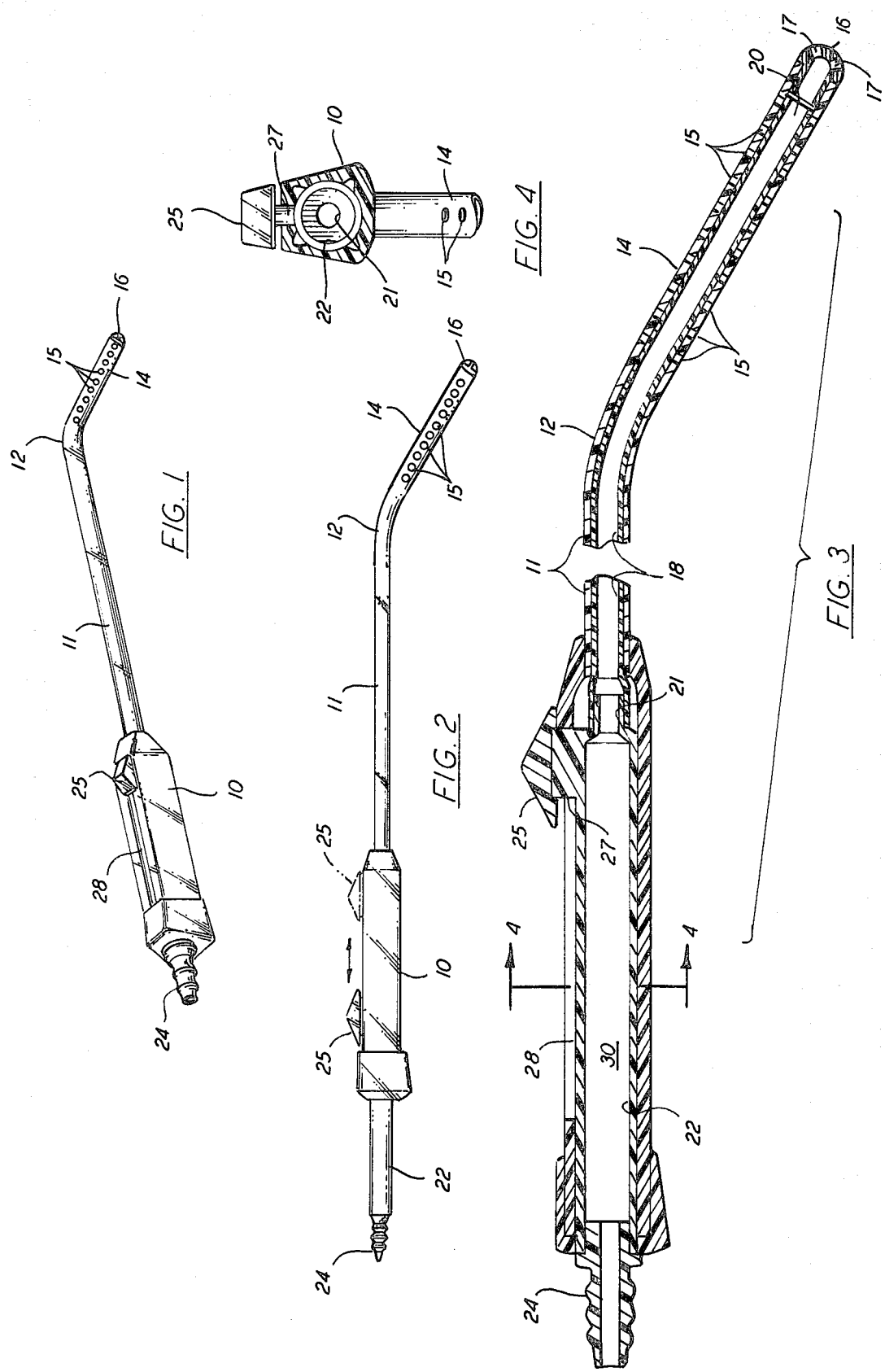

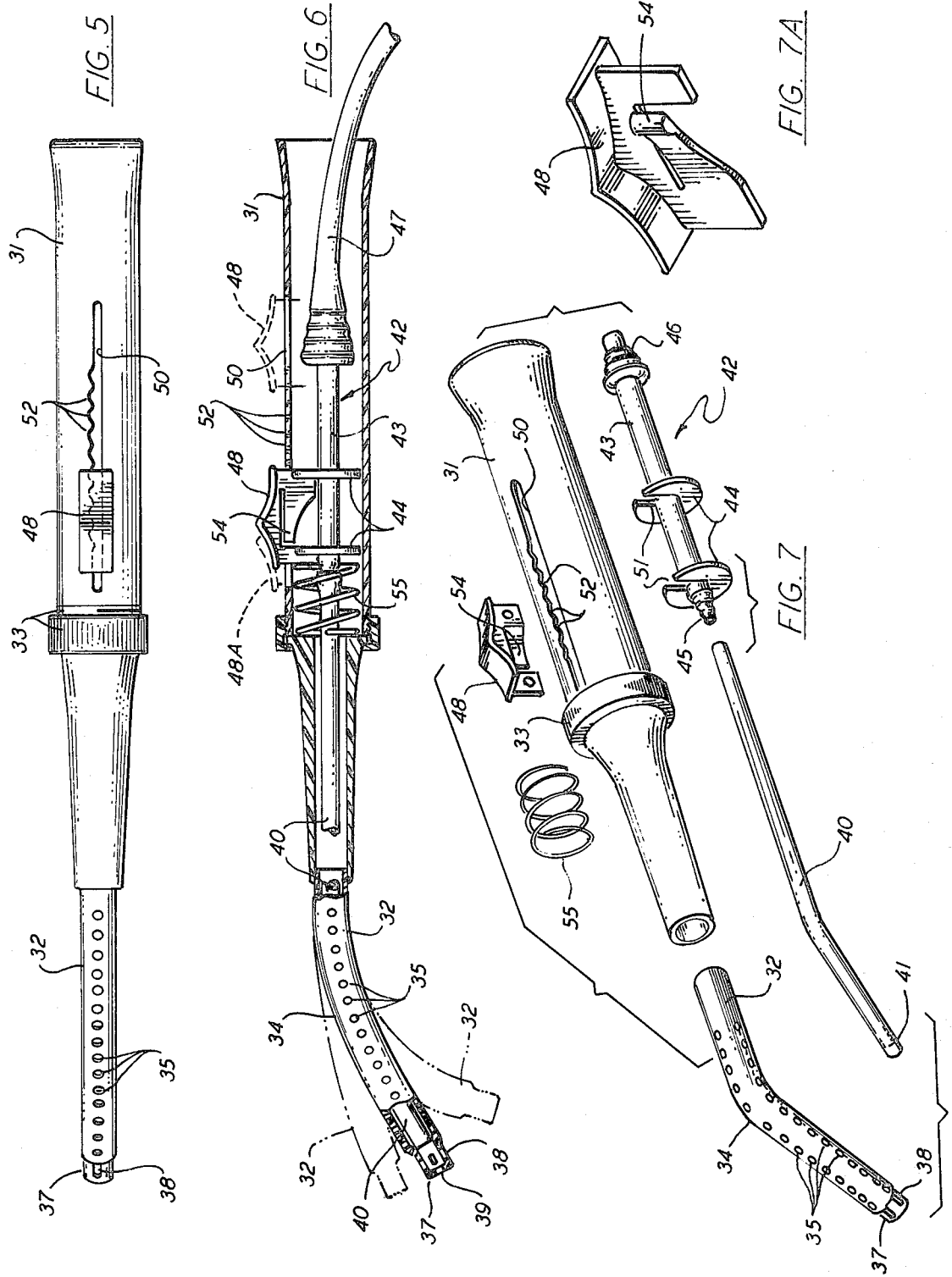

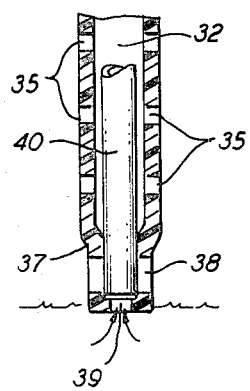 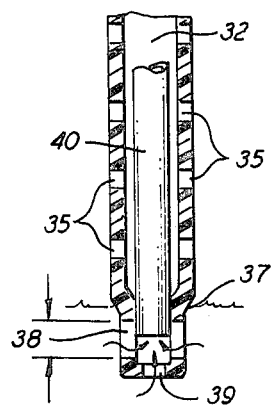 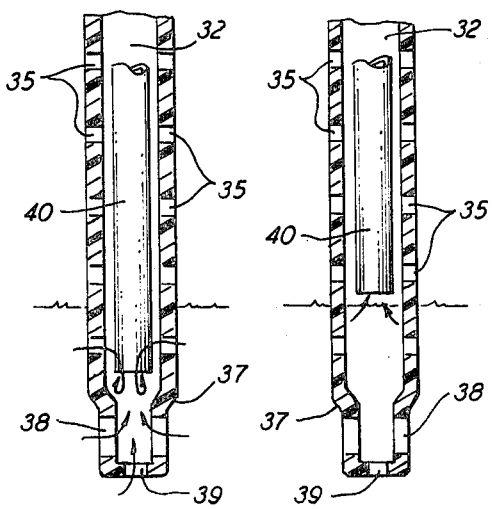
FIG. 8A  FIG. 8B  FIG. 8C  FIG. 8D
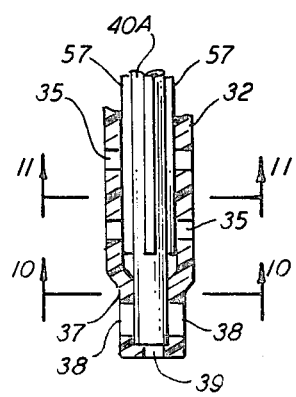 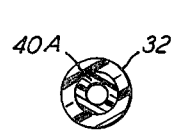 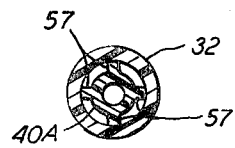
FIG. 9  FIG. 10  FIG. 11
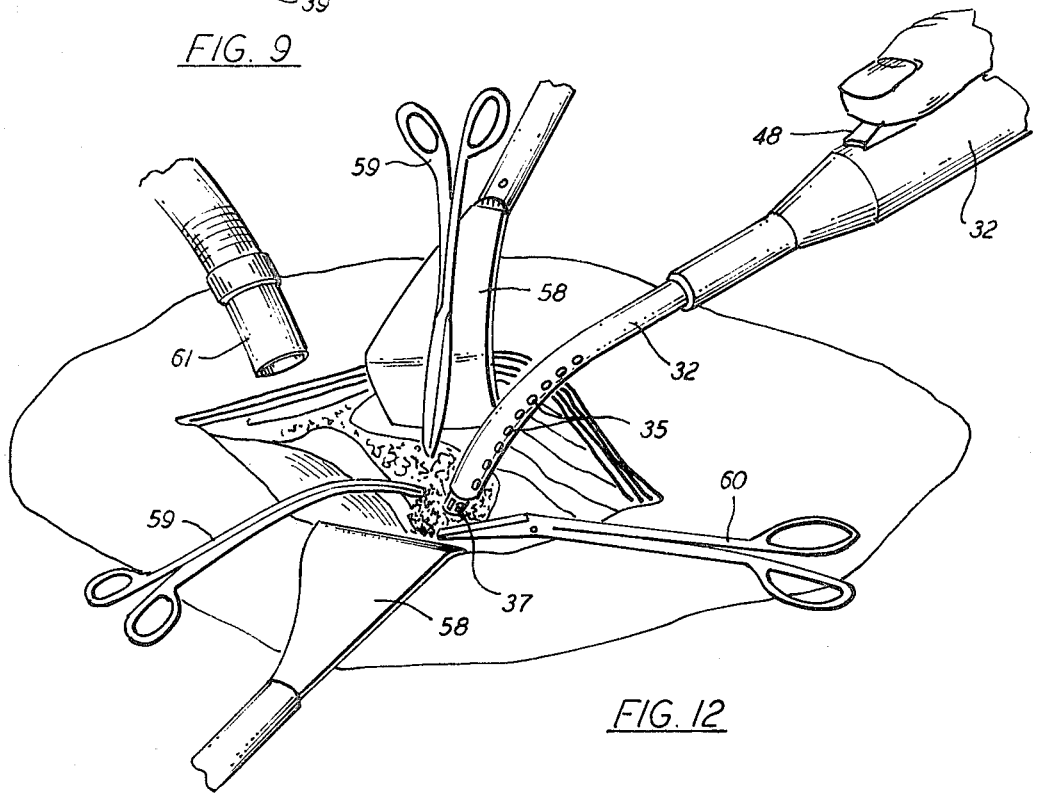
FIG. 12

ADJUSTABLE SUCTION DEVICE FOR MEDICAL USE

RELATED APPLICATION

This application is a continuation-in-part of co-pending application Ser. No. 319,259, filed Nov. 9, 1981 now abandoned by Alan W. Brownlie and Roger D. Spier for ADJUSTABLE SUCTION DEVICE.

BACKGROUND OF THE INVENTION

This invention relates generally to suction devices, and has particular reference to a novel adjustable suction device or aspirator that is particularly adapted for medical use. During open surgical procedure fluids accumulate in the operating field. Their removal is accomplished with a variety of suction devices. Usually these devices include a wand connected by a tube in some manner to a vacuum source, the wand being placed in the incision. The fluids enter the wand through the open end. Factors which should be considered in the design of such suction devices are: I. Minimization of procedural interruption which causes increased duration. II. Reduction of operating field size thereby reducing patient trauma and shock. III. Clear operating field visibility for the surgeon. IV. Reduction of support personel to simplify procedure, reduce cost and increase efficiency. V. Safety to the patient should be considered. The design herin described has been designed to attend to these needs in the following manner: A. Provide remote control of the suction modes it includes which allows noninterruptive changes of mode during the procedure. B. Inclusion of a smaller tip section and an angulated shape to help allow for a minimal sized field. C. An angulated shape which allows the control handle to lie outside the visual cone of the surgeon. D. Inclusion of safety and control feature on both modes to reduce need for attending personnel and protect the patient.

Some suction devices of prior art are designed to drain fluids from a point source or small area and also to drain fluid from a more general area with a strainer system to prevent clogging. To the best of the applicants'. knowledge none of the previously developed devices can remotely and easily adjust the degree or mode of suction in the manner of the present invention. The closest prior art known to the applicants in U.S. Pat. No. 3,426,759 granted Feb. 11, 1969 to W. L. Smith. The Smith patent discloses inner and outer tubes that the specification states can be positioned with respect to one another in either of two positions to provide either fine or gross suctioning. However with the construction disclosed, no matter what the position of adjustment, all of the fluid that is removed must pass through the same fixed number of holes in the inner tube.

Another pertinent patent is U.S. Pat. No. 3,780,740 granted Dec. 25, 1973 to James W. Rhea. This patent discloses an intubation device with the capability of adjusting the number of holes through which fluid can flow into or be drawn from a body cavity. However, the device was not intended for use as an adjustable suction device and its construction is otherwise unlike that of the present invention as will become apparent as the description proceeds. Other pertinent U.S. patents are U.S. Pat. Nos. 1,140,462; 1,188,180; 2,822,808; 3,416,532; 3,590,820; 3,645,497; 3,713,443; 3,834,388; 3,913,577; 3,963,028 and 4,204,328.

SUMMARY OF THE INVENTION

The invention disclosed herein is directed to an adjustable, disposable suction device that is particularly adapted for medical use but is not restricted thereto as it can be advantageously utilized for other applications. In its medical application, the device is used for removing excess blood or body fluids from an open incision during surgery. The device is constructed so that it can drain the fluids from a point source or from a larger general area, and in both cases the device can be adjusted to control how much fluid is removed in a given period of time or to compensate for excessively high available vacuum and irregularities.

The suction device in one embodiment is essentially comprised of a handle, a rigid other tube formed with an oblique bend and a co-acting flexible inner tube. The other tube is connected at one end to the handle and has a plurality of longitudinally spaced radical apertures adjacent its free end. The flexible inner tube is positioned with a close sliding fit in the rigid tube. The inner tube is open at its outer or free end but is otherwise imperforate. With this arrangement, the inner tube can be moved longitudinally within the outer tube to block all of the outer tube apertures or selectively open some or all of them.

The free end of the rigid outer tube is provided with an apertured end cap, and when the inner tube is positioned so as to block the radial apertures of the outer tube the latter can be positioned in an incision so that it removes body fluids from a point source through the end cap. Alternatively, the portion of the outer tube having the radial apertures can be positioned in the incision, and most of all of the apertures can be opened to remove fluids from a general area. The inner tube through which the fluids are removed is adapted to be connected to a vacuum source and means are provided on the handle for manually adjusting the longitudinal position of the tube.

The suction device in another embodiment of the invention differs from the embodiment just described in that the flexible inner tube does not fit the outer tube with a close sliding fit. In this second embodiment there is sufficient clearance between the inner and outer tubes to permit the free flow of fluid between them except when the distal end of the inner tube is moved all of the way to the distal end of the outer tube. The distal end of the outer tube is formed with a reduced diameter portion that closely fits the end of the inner tube and therefore when the latter is moved into the reduced diameter portion fluid can only enter the suction device through a relatively small orifice at the very end of the outer tube. This area is designed to provide progressively greater suction as the tube is adjusted to a position of maximum suction at the end of its travel. This serves to prevent abrupt onset of full suction.

In the second embodiment of the suction device, the handle actuator that controls the longitudinal position of the inner tube within the outer tube is provided with detent means for positive positioning of the inner tube in a number of different positions of adjustment. However, there are no detent means for holding the inner tube at the maximum suction point described above because at that point the suction is capable of harming delicate tissues if left unattended. Accordingly, the actuator must be hand held in this position of adjustment against the action of a compression spring which will return the tube to a safe position upon release of the actuator.

BRIEF DESCRIPTION OF THE DRAWINGS

FIG. 1 is a perspective view of an adjustable suction device embodying the invention;

FIG. 2 is a side elevation of the device of FIG. 1;

FIG. 3 is an enlarged, vertical longitudinal section through the device;

FIG. 4 is a transverse section through the device taken on line 4—4 of FIG. 3;

FIG. 5 is a top plan view of another embodiment of the adjustable suction device of the invention;

FIG. 6 is a side elevation of the suction device of FIG. 5 with parts in section to illustrate details of the construction;

FIG. 7 is an exploded view of the suction device of FIG. 5;

FIG. 7A is an enlarged perspective view of the actuator for the suction device of FIG. 5;

FIGS. 8A-8D inclusive are fragmentary views, partly in section, of the distal end of the device of FIG. 5 showing different positions of adjustment of the inner tube;

FIG. 9 is a fragmentary view corresponding to FIGS. 8A-8D but illustrating a modification in the configuration of the inner tube;

FIGS. 10 and 11 are transverse cross-sectional views taken on lines 10—10 and 11—11 of FIG. 9; and FIG. 12 is a view of a typical surgical field showing the suction device of the invention in use.

DESCRIPTION OF THE PREFERRED EMBODIMENTS

Referring now to the drawings, and with particular reference to FIGS. 1-4, the suction device includes a hollow handle 10 to which one end of a rigid tube 11 is secured. The tube 11 is bent at 12 so that a portion 14 of the tube adjacent its outer or free end is disposed at an oblique angle to the remainder of the tube. The portion 14 of the tube is provided with one or more rows of longitudinally spaced radial apertures 15, there being two diametrically opposite rows in the illustrated embodiment. The free end of tube 11 is also preferably fitted with an end cap 16 having apertures 17. The end cap is rounded as best shown in FIG. 3 and its outer surface merges smoothly with that of the tube.

A flexible tube 18 is positioned with a close sliding fit in the rigid tube 11 so that it can be moved longitudinally with respect to the latter. The flexible tube, which is substantially coextensive with the rigid tube, is open at its outer end 20 but is otherwise imperforate having no radial apertures or holes throughout its length.

The inner end of the flexible tube 18 is secured to a serrated or threaded fitting 21 at one end of a hollow slide member 22 that is slidably mounted in the hollow handle 10. The other end of the slide member is provided with a standard fitting 24 for the attachment to a suitable vacuum source through flexible tubing (not shown). The slide member can be moved back and forth relative to the handle 10 by a thumb piece 25, FIG. 3, that is secured to the outer end of a narrow rib 27 that is integral with the slide member and projects outwardly therefrom through a longitudinal slot 28 in the handle.

When the thumb piece 25 is at the forward end of slot 28, or right end as shown in FIG. 3, the outer end 20 of the flexible tube 18 will extend almost to the end of rigid tube 11 and all of the radial apertures 15 of the latter will be blocked by the flexible tube so that they are effectively closed. In this condition, fluids can only enter the suction device through the end cap apertures 17, the fluids being drawn through the flexible tube into the interior 30 of the slide member 22 and from thence out through the fitting 24.

With the radial apertures blocked so that fluid cannot pass through them, the device is particularly adapted for removing fluids from a point source, the device being positioned in the incision so that the end cap 16 is brought into contact with the point source of the fluids.

When the thumb piece 25 is moved to the rear or left end of the slot 28 as indicated in FIG. 2, the inner, flexible tube 18 will be moved back from the free end of the outer, rigid tube 11 opening its radial apertures 15. In this condition, fluids can be drawn into the device through all of the radial apertures and a general area can be drained by positioning the device so that the obliquely extending portion 14 of the rigid tube is lying in that general area, the bend in the tube facilitating the positioning of the device in this manner. As noted hereinbefore, when the suction device is draining a general area of an incision, the amount of fluid that is removed in a given period of time can be controlled by selectively moving the thumb piece 25 to open more or less of the radial apertures.

FIGS. 5-8D illustrate another embodiment of the adjustable suction device. In this embodiment, the device includes a hollow, open-ended handle 31 one end of which is releasably secured to an outer suction tube or tip 32 by means of a threaded connection 33. The outer tube 32 can be rigid and formed with a permanent bend as shown at 34 in FIGS. 6 and 7, or it can be semi-rigid. A semi-rigid tube can be bent to any angle desired and will maintain its position until further force is applied to change its configuration.

The outer tube 32 is provided with a plurality of rows of longitudinally spaced radial apertures 35. At its distal end below its radial apertures 35, the tube is formed with a reduced diameter portion 37, FIG. 6, that has a number of radially disposed elongated apertures or slots 38. The outer end of the reduced diameter portion 37 is closed except for a relatively small aperture 39, FIGS. 6 and 8A-8D.

A flexible inner tube 40 of uniform diameter is positioned in the outer tube 32 and is movable longitudinally with respect thereto. The flexible tube is substantially coextensive with the rigid tube and is open at its outer end 41, FIG. 7, but is otherwise imperforate. As best shown in FIGS. 8C and 8D, there is clearance between the outside diameter of the inner tube 40 and the inside diameter of the outer tube except at the reduced diameter portion 37 of the outer tube. The clearance between the tubes permits the free flow of fluid between them. However, when the distal end 41 of the inner tube 40 is moved into the reduced diameter portion of the outer tube, as shown in FIG. 8A, it fits the latter with a very close sliding fit and there is no fluid flow between the tubes above the reduced diameter portion as will be explained in more detail hereinafter.

Positioned in the hollow handle 31 is a longitudinally movable slide member 42, FIGS. 6 and 7, comprised of a hollow tube 43 on which are mounted a pair of discs 44 for guiding the member during its back and forth sliding movement. The tube 43 is provided with standard fittings 45,46 at its ends and the inner end of the flexible inner tube 40 is connected to the fitting 45 while the other fitting is connected to a tube or conduit 47 leading to the hospital vacuum source (not shown).

The slide member 42 can be moved back and forth relative to the handle 31 by means of a thumb piece actuator 48, FIGS. 5-7. The lower part of the actuator passes through a longitudinal slot 50 in the handle and snaps into slots 51 in the discs 44. As best shown in FIGS. 5 and 7, the handle slot 50 is formed along one edge with a series of indentations 52 any one of which can be engaged by a resilient detent 54, FIGS. 7 and 7A, that is an integral part of the actuator 48. The configuration of the actuator as shown in FIG. 7A together with the resiliency of the material from which the actuator is made impart resiliency to the detent.

The actuator detent 54 and coacting slot indentations 52 give the actuator a relatively large number of discrete positions of adjustment and this in turn permits the position of the flexible inner tube 40 to be precisely adjusted relative to the outer tube 32. In this connection, it may be seen from FIG. 6 that when actuator 48 is positioned so that its detent is in the forwardmost indentation 52, or farthest to the left as viewed in FIGS. 5 and 6, the distal end of the inner tube is located so that it is just short of entering the reduced diameter portion 37 of the outer tube 32.

There is no indentation 52 for maintaining the position of the inner tube when its distal end is moved all the way into the reduced diameter portion 37 as shown in FIG. 8A because in this position only the small aperture 39 at the end of the outer tube is open and the suction through this single aperture would be strong enough to damage delicate tissues. For this reason, the actuator 48 must be manually held in its forwardmost position, shown in dash lines at 48A in FIG. 6, against the action of a compression spring 55 to hold the end of the inner tube in engagement with the end of the outer tube, FIG. 8A, and permit suction through the aperture 39 only.

The construction just described gives the suction device great versatility in use as may be seen from FIGS. 8 and 12. When the flexible inner tube 40 is positioned so that its distal end is moved all the way into the reduced diameter portion 37 of the outer tube 32, FIG. 8A, there is maximum suction through the relatively small end aperture 39. This is designated the full spot position of the device where drainage is from a point source and it enables very rapid removal of fluids from a discrete point. In this mode, the device can be used to remove fluid flowing rapidly from a small blood vessel, or for removing discrete pools of fluid from a limited source, or for removing small bone chips or the like. The disadvantage of using the suction device in this mode is that the suction is so great that it can cause damage to delicate tissues.

If the inner tube 40 is retracted or moved rearwardly a small distance as indicated in FIG. 8B, portions of the slots 38 become exposed and because of the larger number of exposed apertures the suction at each is reduced. In this mode, the device can still rapidly remove fluids from small pools but there is less likelihood of damaging delicate tissues. Further retraction of the inner tube 40 to a position as shown for example in FIGS. 8C or 8D exposes some or all of the radial apertures 35 and permits drainage to take place in a larger pool or area but the suction at the individual apertures is further reduced.

FIGS. 9-11 illustrate a modification in the configuration of the flexible inner tube 40. In this modification, the tube 40A is provided with a plurality of outwardly projecting, radial ribs 57 that operate to center the inner tube in the outer tube 32. As best shown in FIG. 9, the ribs 57 do not extend all the way to the distal end of tube 40A thus enabling the latter to be moved into the reduced diameter port 37 of the outer tube as described above in connection with FIG. 8A.

FIG. 12 illustrates the suction device of the invention in use in a typical surgical field. In performing the surgery, the field is invariably crowded with other instruments and devices such as retractors 58, hemostats 59, surgical scissors 60 and a close light source 61. In this illustration, the suction device is shown in the full spot position or mode but it will be apparent that if the inner tube 40 is retracted as described in connection with FIGS. 8C and D and the device is rotated approximately 90° in either direction, the angled distal end of outer tube 32 will lie in the field and effect drainage from a considerably larger area. The configuration of the surgical device is advantageous because it can be positioned out of the direct line of vision of the surgeon. Another very desirable feature is the ability to adjust the position of the inner tube, and thus the degree and extent of the suction, from a point remote from the surgical field by means of the handle actuator 48.

In its medical application, the above described suction device can be advantageously utilized for general surgery, thoracic, vascular and orthopedic surgery including arthroscopy; also, other applied fields of surgery including dental and veterinary surgery. The components of the device are made of plastic and it is intended that it be disposable. Nonetheless, the device has a rugged construction and feels and functions like a permanent surgical instrument. The relatively long rows of radial apertures 15 minimize the undesirable effects of clogging because if some of the apertures become clogged additional apertures can be opened to compensate.

From the foregoing description it will be apparent that the invention provides a novel and versatile medical instrument. As will be understood by those familiar with the art, the invention may be embodied in other specific forms without departing from the spirit or essential characteristics thereof.

We claim:

1. An adjustable, disposable suction device comprising a hollow handle, an elongated substantially rigid outer tube connected at one end to the handle, the rigid tube having a plurality of longitudinally spaced radial apertures adjacent its free end, an imperforate flexible inner tube positioned in the rigid tube, there being clearance between the flexible and rigid tubes to permit the flow of fluid therebetween, the flexible tube being substantially coextensive with the rigid tube and being movable longitudinally within the latter so that it is operable to block all of the radial apertures in the rigid tube or selectively open some or all of them, a hollow slide member mounted in the handle for longitudinal movement relative thereto, the slide member being connected at one end of the flexible tube with the interiors of the tube and member being in communication with one another, coupling means at the other end of the hollow slide member for connecting its interior with a vacuum source, and means on the slide member for manually moving it back and forth and thereby move the flexible tube to open or close the radial apertures in the rigid tube, the free end of the rigid outer tube having a reduced diameter portion into which the free end of the flexible inner tube can be moved, the inner tube being received in the outer tube reduced diameter portion with a close sliding fit whereby the inner tube operates to block the radial apertures in the outer tube when its free end is positioned in the reduced diameter portion of the outer tube.

2. A suction device as defined in claim 1 wherein the free end of the rigid outer tube is closed except for a small aperture that is not blocked by the flexible inner tube when the free end of the latter is positioned in the reduced diameter portion of the outer tube.

3. An adjustable, disposable suction device comprising a hollow handle, an elongated substantially rigid outer tube connected at one end to the handle, the rigid tube having a plurality of longitudinally spaced radial apertures adjacent its free end, an imperforate flexible inner tube positioned in the rigid tube, the tubes being dimensioned so that there is clearance between the outer diameter of the flexible tube and inner diameter of the rigid tube sufficient to permit the flow of fluid therebetween, the flexible tube being movable longitudinally within the rigid tube, means for connecting the inner end of the flexible tube to vacuum source, the free end of the rigid tube being formed below its radial apertures with a reduced diameter portion into which the outer, free end of the flexible tube can be moved, the flexible tube being received in the reduced diameter portion with a close sliding fit so that when it is positioned therein suction in the flexible tube cannot operate to draw fluids into the rigid tube through the radial apertures, withdrawal of the flexible tube from the reduced diameter portion of the rigid tube permitting fluid to be drawn into the tubes through the radial apertures.

4. A suction device as defined in claim 3 wherein the free end of the rigid outer tube is closed except for a small aperture that is not blocked by the flexible inner tube when the free end of the latter is positioned in the reduced diameter portion of the outer tube.

5. A suction device as defined in claim 4 wherein the reduced diameter portion of the rigid tube has at least one aperture in its sidewall.

6. A suction device as defined in claim 3 wherein the means for connecting the inner end of the flexible tube to a vacuum source is a hollow slide member mounted in the handle for longitudinal movement relative thereto, the slide member being connected at one end to the flexible tube and having coupling means at its other end for connecting it to a vacuum source.

7. A suction device as defined in claim 6 together with an actuator connected to the slide member for manually moving it back and forth whereby the flexible tube is moved longitudinally within the rigid tube.

8. A suction device as defined in claim 7 together with coacting detent means on the actuator and handle for releasably holding the flexible tube in a plurality of different positions of adjustment in the rigid tube.

* * * * *